(12) United States Patent
Schoenmakers et al.

(10) Patent No.: US 8,912,491 B2
(45) Date of Patent: Dec. 16, 2014

(54) METHOD OF PERFORMING TOMOGRAPHIC IMAGING OF A SAMPLE IN A CHARGED-PARTICLE MICROSCOPE

(71) Applicant: FEI Company, Hillsboro, OR (US)

(72) Inventors: Remco Schoenmakers, Best (NL); Uwe Luecken, Eindhoven (NL); Erik Michiel Franken, Nuenen (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/091,035

(22) Filed: Nov. 26, 2013

(65) Prior Publication Data
US 2014/0145077 A1    May 29, 2014

Related U.S. Application Data

(60) Provisional application No. 61/731,162, filed on Nov. 29, 2012.

(30) Foreign Application Priority Data

Nov. 29, 2012  (EP) ..................................... 12194825

(51) Int. Cl.
*G01N 23/00*    (2006.01)
(Continued)

(52) U.S. Cl.
CPC ................. *H01J 37/22* (2013.01); *H01J 37/26* (2013.01);
(Continued)

(58) Field of Classification Search
USPC .................................. 250/306, 307, 310, 311
See application file for complete search history.

(56) References Cited

U.S. PATENT DOCUMENTS 7,154,092 B2    12/2006    Furukawa
7,825,378 B2    11/2010    Yakushevska et al.
(Continued)

FOREIGN PATENT DOCUMENTS

EP        2309459        4/2011
WO        2011033097     3/2011

OTHER PUBLICATIONS

Florea, Ileana, et al., "3D Analysis of the Morphology and Spatial Distribution of Nitrogen in Nitrogen-Doped Carbon Nanotubes by Energy-Filtered Transmission Electron Microscopy Tomography," J. Am. Chem. Soc., May 22, 2012, pp. 9672-9680, vol. 134.

(Continued)

*Primary Examiner* — Nikita Wells
*Assistant Examiner* — Meenakshi Sahu
(74) *Attorney, Agent, or Firm* — Scheinberg & Associates, PC; Michael O. Scheinberg

(57) ABSTRACT

The invention relates to a method of performing tomographic imaging of a sample comprising providing a beam of charged particles; providing the sample on a sample holder that can be tilted; in an imaging step, directing the beam through the sample to image the sample; repeating this procedure at each of a series of sample tilts to acquire a set of images; in a reconstruction step, mathematically processing images from said set to construct a composite image, whereby in said imaging step, for a given sample tilt, a sequence of component images is captured at a corresponding sequence of focus settings; and in said reconstruction step, for at least one member of said series of sample tilts, multiple members of said sequence of component images are used in said mathematical image processing. This renders a 3D imaging cube rather than a 2D imaging sheet at a given sample tilt.

18 Claims, 3 Drawing Sheets

Figure 1:
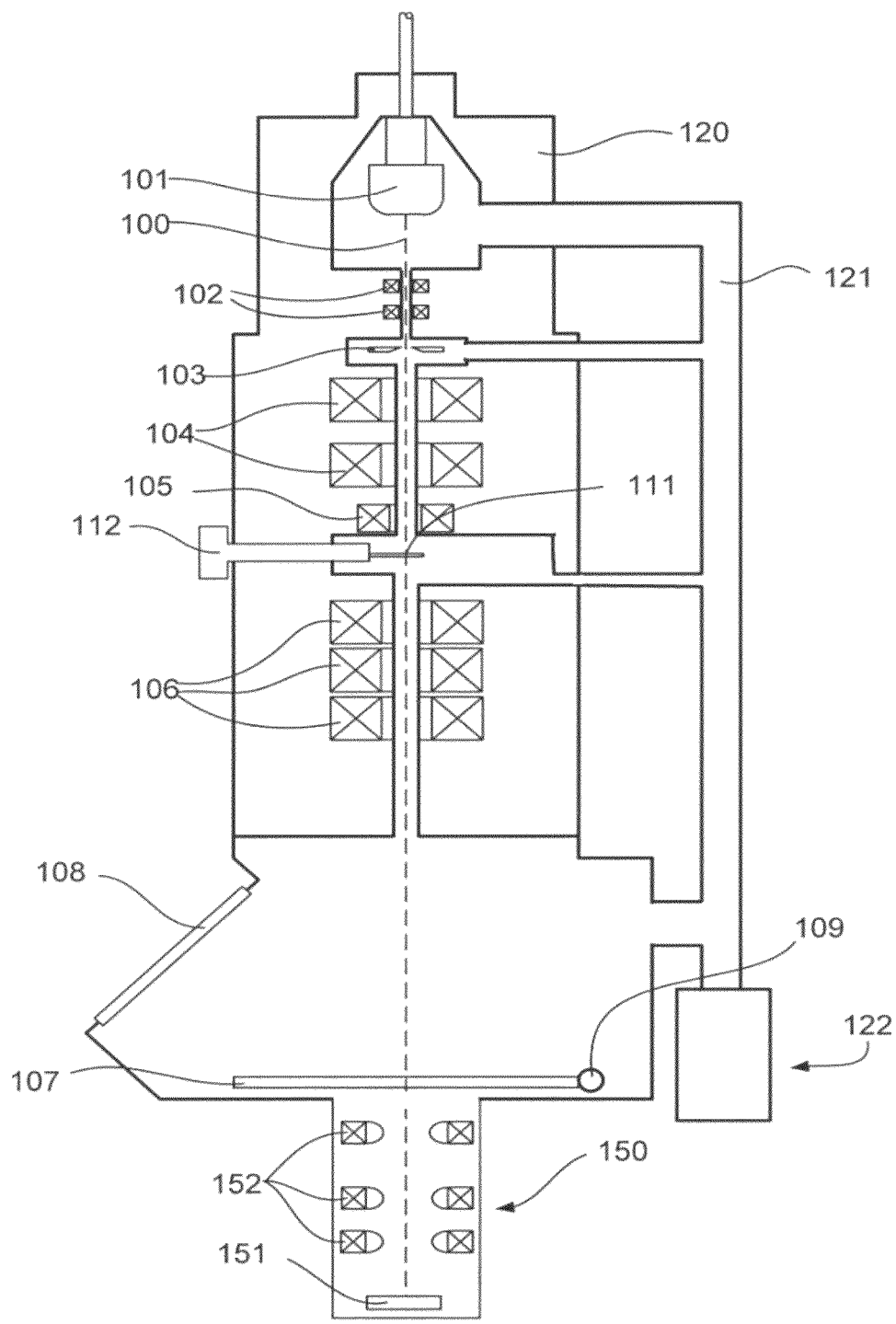

(51) Int. Cl.
*G21K 7/00* (2006.01)
*H01J 37/26* (2006.01)
*H01J 37/22* (2006.01)
*G01N 23/04* (2006.01)
*H01J 37/21* (2006.01)
*G01N 23/225* (2006.01)

(52) U.S. Cl.
CPC ........ H01J 37/222 (2013.01); *G01N 2223/418* (2013.01); *H01J 2237/2802* (2013.01); *H01J 2237/21* (2013.01); G01N 23/046 (2013.01); *H01J 2237/226* (2013.01); H01J 37/21 (2013.01); G01N 23/2251 (2013.01)
USPC ............ 250/307; 250/306; 250/310; 250/311

(56) References Cited

U.S. PATENT DOCUMENTS

| | | |
|---|---|---|
| 8,080,791 B2 | 12/2011 | von Harrach et al. |
| 8,232,523 B2 | 7/2012 | Bourghorbel et al. |
| 2006/0038127 A1* | 2/2006 | Furukawa ................ 250/311 |
| 2012/0292503 A1 | 11/2012 | Phifer, Jr. et al. |
| 2013/0037714 A1 | 2/2013 | Boughorbel et al. |
| 2013/0037715 A1 | 2/2013 | Boughorbel et al. |

OTHER PUBLICATIONS

Kubel, Christian, et al., "Recent Advances in Electron Tomography: TEM and HAADF-STEM Tomography for Materials Science and Semiconductor Applications," Microsc. Microanal. 2005, pp. 378-400, vol. 11.

Saghi, Z., et al., "Hybrid Tomography of Nanostructures in the Electron Microscope," Mater. Res. Soc. Symp. Proc. 2009, 6 pages, vol. 1184.

Van Den Broek, W., et al., "A model based reconstruction technique for depth sectioning with scanning transmission electron microscopy," Ultramicroscopy, 2010, pp. 548-554, vol. 110.

Kubel, Christian, et al., "Recent Advances in Electron Tomography: TEM and HAADF-STEM Tomography for Materials Science and Semiconductor Applications," Microsc. Microanal., 2005, pp. 378-400, vol. 11.

* cited by examiner

METHOD OF PERFORMING TOMOGRAPHIC IMAGING OF A SAMPLE IN A CHARGED-PARTICLE MICROSCOPE

The invention relates to a method of performing tomographic imaging of a sample in a charged-particle microscope, comprising the following steps:
- Providing a beam of charged particles that propagate along a particle-optical axis;
- Providing the sample on a sample holder that can be tilted relative to said beam;
- In an imaging step, directing the beam through the sample so as to form and capture an image of the sample at an image detector;
- Repeating this procedure at each of a series of sample tilts so as to acquire a corresponding set of images;
- In a reconstruction step, mathematically processing images from said set so as to construct a composite image of the sample.

The invention also relates to a charged-particle microscope comprising:
- A charged-particle source, for producing a charged-particle beam that propagates along a particle-optical axis;
- A sample holder, for holding and positioning a sample;
- A charged-particle lens system, for directing said beam through the sample so as to form an image of the sample;
- An image detector, for capturing said image in an imaging step;
- Apparatus for adjusting a focus setting of the beam relative to the sample;
- A computer processor, for mathematically processing input images in a reconstruction step, so as to form an output reconstructed image.

For purposes of clarity and consistency, the following terms as used throughout this text and the appended claims should be interpreted as follows:
- The term "charged particle" encompasses an electron or ion (generally a positive ion, such as a Gallium ion or Helium ion, for example, though a negative ion is also possible). It may also be a proton, for example.
- The term "charged-particle microscope" (CPM) refers to an apparatus that uses a charged-particle beam to create a magnified image of an object, feature or component that is generally too small to be seen in satisfactory detail with the naked human eye. In addition to having an imaging functionality, such an apparatus may also have a machining functionality; for example, it may be used to locally modify a sample by removing material therefrom ("milling" or "ablation") or adding material thereto ("deposition"). Said imaging functionality and machining functionality may be provided by the same type of charged particle, or may be provided by different types of charged particle; for example, a Focused Ion Beam (FIB) microscope may employ a (focused) ion beam for machining purposes and an electron beam for imaging purposes (a so-called "dual beam" microscope), or it may perform machining with a relatively high-energy ion beam and perform imaging with a relatively low-energy ion beam.
- The term "sample holder" refers to any type of table, platform, arm, etc., upon which a sample can be mounted and held in place. Generally, such a sample holder will be comprised in a stage assembly, with which it can be accurately positioned in several degrees of freedom, e.g. with the aid of electrical actuators.
- The term "charged-particle lens system" refers to a system of one or more electrostatic and/or magnetic lenses that can be used to manipulate a charged-particle beam, serving to provide it with a certain focus or deflection, for example, and/or to mitigate one or more aberrations therein. In addition to (various types of) conventional lens elements, the charged-particle lens system (particle-optical column) may also comprise elements such as deflectors, stigmators, multipoles, aperture (pupil) plates, etc.
- The "series of different sample tilts" referred to here may take different forms. In particular, the tilt increments between successive members of such a series may be equal or unequal (or mixtures of these). Examples of scenarios with unequal tilt increments include EST (Equal Slope Tomography), in which the slope (tangent of tilt) undergoes equal increments, and the so-called Saxton tilt increment scheme, in which smaller tilt increments are used as one progresses toward larger tilt values (measured with respect to the sample surface). In addition to referring to the angle between the charged-particle beam and the plane of the sample surface (altitude angle), the term "tilt" may also refer to the azimuth angle, i.e. the rotational stance of the sample about the particle-optical axis intersecting it. A change in tilt value may thus encompass one or more discrete rotations of the sample about this axis (e.g. as in the case of so-called "dual axis", "multiple axis" and "conical tilt" tomography). The number of increments in a tilt series is generally discretionary.

Such concepts will be familiar to the skilled artisan.

In what follows, the invention will—by way of example—often be set forth in the specific context of electron microscopes. However, such simplification is intended solely for clarity/illustrative purposes, and should not be interpreted as limiting.

Electron microscopy is a well-known technique for imaging microscopic objects. The basic genus of electron microscope has undergone evolution into a number of well-known apparatus species, such as the Transmission Electron Microscope (TEM), Scanning Electron Microscope (SEM), and Scanning Transmission Electron Microscope (STEM), and also into various sub-species, such as so-called "dual-beam" tools (e.g. a FIB-SEM), which additionally employ a "machining" beam of ions, allowing supportive activities such as ion-beam milling or ion-beam-induced deposition, for example. In traditional electron microscopes, the imaging beam is "on" for an extended period of time during a given imaging session; however, electron microscopes are also available in which imaging occurs on the basis of a relatively short "flash" or "burst" of electrons, such an approach being of potential benefit when attempting to image moving samples or radiation-sensitive specimens, for example. It should be noted that a STEM may be a dedicated tool, or it may be a TEM that is used in so-called "scanning mode" (enabled by the use of certain (dedicated) deflectors/detectors/software, for example).

The current invention is of relevance to CPMs in which the employed charged-particle beam passes through the sample, as in the case of a TEM or STEM, for example. In order to be (sufficiently) transmissive to the beam, the sample must be relatively thin (e.g. of the order of about a tenth of a micron to several microns, depending on the material involved) and the employed charged particles are generally accelerated to relatively high energies (e.g. of the order of about 1-500 keV, or even energies in the MeV range). However, though one might consider such thin samples to be essentially two-dimensional (2D), there will still generally be significant three-dimensional (3D) information within them. For example, a typical biological cell is an exceptionally thin object, but it still contains detailed internal structure within its volume; viewing such structure with a conventional TEM (or STEM) renders a 2D projection of this 3D information, with resultant loss of volume information. Put another way, charged particles transmitted through such a sample will contain contrast information from various depths within the sample, but this information will be convoluted in the resulting 2D image. Although this may be acceptable in certain applications (e.g. approximate identification of types/shapes of general structures present), it will not meet the required standard in other, more critical applications (e.g. where detailed imagery of a mitochondrion within a cell is required). Although biological examples are mentioned here (by way of illustration), similar considerations will apply in other fields, such as mineralogy/petrology, metallurgy and semiconductor manufacturing, for example.

To address this problem, one can contemplate the use of tomographic transmission microscopy. In this approach, in order to "disentangle" (spatially resolve) the convoluted image referred to above, some form of parallax data will be required, so as to be able to distinguish between foreground and background features in the sample. Such parallax data can be provided by imaging the sample at a variety of different tilts with respect to the incoming charged-particle beam—which is equivalent to looking at the sample along a variety of different lines of sight. In order to perform the actual deconvolution of this tilt-differentiated set of images into a depth-resolved composite image, mathematical processing referred to as "reconstruction" is required. However, although such an approach succeeds in producing 3D (composite) imagery of a sample, the resolution of that imagery has, up to now, generally proved to be rather disappointing.

It is an object of the invention to address this issue. More specifically, it is an object of the invention to provide a method that can be used to more satisfactorily perform transmission charged-particle microscopy on samples that comprise relatively fine volume structures. Moreover, it is an object of the invention that said method should be more accurate and/or versatile than conventional tomographic transmission microscopy.

These and other objects are achieved in a method as specified in the opening paragraph, characterized in that:
In said imaging step, for a given sample tilt, a sequence of component images is captured at a corresponding sequence of focus settings;
In said reconstruction step, for at least one member of said series of sample tilts, multiple members of said sequence of component images are used in said mathematical image processing.

They are equally achieved in an apparatus as set forth in the second opening paragraph above, characterized in that the apparatus comprises a controller that can be invoked (programmed) to perform the following operations:
In said imaging step, for a given sample tilt, capturing a sequence of component images at a corresponding sequence of focus settings;
In said reconstruction step, for at least one member of said series of sample tilts, performing said mathematical image processing using multiple members of said sequence of component images.

For good order, it should be noted that the term "focus setting" as here employed refers to the position of a focal point of the beam relative to a given reference level in the sample (a plane through a given reference point, oriented perpendicular to the particle-optical axis). Such a focus setting can, for example, be adjusted by using one or more of the following methods:
Altering a focal power of at least one lens element used to focus the beam (which may include turning an assistive lens element on or off, for example).
Altering the position of the sample along the particle-optical axis (e.g. using a piezoelectric actuator).
Altering the position of at least one lens element along the particle-optical axis.

The skilled artisan will readily grasp these concepts.

According to the invention, by employing a sequence of focus settings and capturing a corresponding sequence of component images at each sample tilt value, one can realize a number of substantial advantages. To explain these more fully, use will be made of a Cartesian coordinate system in which:
The z-axis lies along the direction of the particle-optical axis of the beam;
The x-axis lies along the tilt axis of the sample.

One then obtains the following insights.
Traditionally, because each imaging step is performed on a tilted sample, not all parts of the sample can simultaneously have a given focus state (e.g. in-focus, or a given degree of defocus); in principle, for a given focus state, only one y-coordinate on the sample will have that state. Accordingly, in prior-art transmission tomography, a mathematically reconstructed image of a given (subsurface) "layer" or "level" of the sample will typically demonstrate sub-optimal resolution and an erratic power spectrum (basically as a result of processing data with mixed degrees of "blurring"). However, if, in accordance with the current invention, focus setting is varied during each imaging step, then one can capture a 3D imaging cube that will allow a plurality of y-coordinates $\{C_y\}$ on the sample to be reconstructed for a selection of focus states. What this means in practice is that, using the current invention:
A given layer/level can now be reconstructed so as to exhibit an essentially uniform focus state, with substantially higher resolution and a more consistent power spectrum.
It becomes possible to choose the focus state at which a given layer/level is reconstructed. For example, one may now reconstruct an image of a given layer/level at best focus and also at a variety of degrees (and/or signs) of de-focus.

So as to exploit this advantage to best effect, the extremities and increment size of the employed sequence of focus settings can be planned in an intelligent manner. For example, one may advantageously choose the employed focus range (i.e. the range of focus settings traversed during a given imaging step) so as to encompass the z-direction spatial extent of the tilted sample (i.e. the difference in z-coordinates between the highest and lowest points of the tilt plane of the sample); in this way, the inventive image reconstruction described above can be applied to the entire y-extent of the sample. Moreover, the smaller the increments between adjacent focus settings in a given focus sequence, the better will be the resolution of the inventive image reconstruction (the closer neighboring points in $\{C_y\}$ will be to one another).

Another advantage concerns the Signal-to-Noise Ratio (SNR) of the obtained imagery.

For a given sample tilt, the SNR of a component image of the inventive 3D imaging cube will be comparable to the SNR of a prior-art single-focus image with the same exposure time. However, by adding together several component images from the inventive 3D imaging cube, the SNR can be improved. In a simple scenario, "straightforward" addition can be employed, which, however, will generally cause a certain blurring effect due to the different focus settings per component image. However, in a more sophisticated approach, component images are summed in a manner that takes into account the Contrast Transfer Function (CTF) of each component image—leading to improved SNR without significant blurring. The skilled artisan will be familiar with the concept of a CTF, which is elucidated in more detail in the following reference, for example: http://en.wikipedia.org/wiki/Contrast_transfer_function Yet another advantage may be elucidated as follows. By treating focus as a variable and gathering imaging data as a function thereof, one is increasing the number of floating parameters that can be used to solve the aforementioned mathematical deconvolution/reconstruction problem. One may liken this, to some extent, to a problem in which several simultaneous equations need to be solved, but the number of variables exceeds the available number of equations; increasing the number of equations will serve to reduce the size of the corresponding solution space, and, accordingly, simplify the problem to be solved.

These and other advantages will be set forth in more detail below.

According to the current invention, the imaging step at a given sample tilt will involve capturing a whole sequence of component images at different focus settings rather than just a single image. However, if a relatively fast/sensitive detector is employed (e.g. a suitable CMOS detector), then the duration of the inventive imaging step, and the total dose to which the sample is exposed, need not be prohibitively increased relative to the single-image scenario of the prior art.

In a particular embodiment of the current invention, the relative position of the particle-optical axis and the sample is kept substantially constant during said imaging step; in other words, the imaging step does not involve a scanning movement of the beam along the surface of the sample. This is the situation in a TEM, for example. However, the invention also lends itself to application in a scenario whereby, during said imaging step, the relative position of the particle-optical axis and the sample is varied by causing the beam to scan along the sample. Such a scenario occurs, for example, in the case of:

A STEM. This resembles a conventional TEM in that it employs transmissive microscopy, but also somewhat resembles a SEM in that it builds up an image by scanning a relatively narrow beam across a sample. The beam diameter in a STEM is typically of the order of a single pixel wide.

A so-called TEM Spot Scan. This is intermediate between a TEM and a STEM, in that it performs beam scanning (like a STEM) but uses a wider beam (larger than a single pixel, but smaller than the (parallel-illuminated) full field of view of a TEM).

In scanning-based scenarios such as these, the imaging step may be carried out in different ways. For example:

One can choose a given focus setting $F_n$, maintain this focus setting for the duration of a scanning sweep of the beam w.r.t. the sample, then choose the next focus setting $F_{n+1}$, perform another scanning sweep of the beam, and so forth for subsequent focus settings $F_{n+2}$, $F_{n+3}$, etc.

Alternatively, for a given point on the sample, one can capture a sequence of component images at a sequence of focus settings $[F_n]$, then move onto an adjacent point on the sample and capture another sequence of component images for the sequence $[F_n]$, and so forth for each subsequent point along a scanning path of the beam. It should be noted in this context that (an objective lens in) a typical particle-optical lens system will generally exhibit hysteresis, and, accordingly, if the focus settings are varied by making adjustments to the power of (elements of) such a lens system, the sequence $[F_n]$ should preferably be traversed in the same direction for each point on the scan path, e.g. starting with a "high focus" and moving the focal point downward (from the beam entrance surface toward the beam emergence surface of the sample). The same general argument applies to a situation whereby focus settings are varied by moving the sample holder—although, in this case, it is conceivable that, as actuator design/performance improves, hysteresis will become less of an issue. In the case of a STEM, focus settings can be altered via appropriate adjustments to the condenser lens, which typically exhibits substantially less hysteresis than an objective lens.

It should be noted that, in the current invention, the increments between successive members of the sequence of focus settings $[F_n]$ need not necessarily be constant; if so desired, these increments may instead have variable values. It should also be noted that the cardinality (number of members) of the sequence of focus settings $[F_n]$ need not necessarily be a constant for each employed tilt value of the sample; instead, if desired, the sequence $[F_n]$ may contain a different number of focus settings for (one or more) different sample tilt values (as long as the cardinality of each sequence $[F_n]$ is greater than 1). As a further possibility, one may choose to apply a "mixed approach" in which the current invention is applied at certain tilt values of the sample, but a conventional single measurement is made at certain other tilt values of the sample (e.g. at or proximal to zero tilt). In a particular "maximum data" approach, for each member of said series of sample tilts, all of the captured component images are used in said mathematical image processing; however, the invention also allows certain component images to be left out of the reconstruction process, if desired. All such scenarios fall within the scope of the appended claims.

Capturing a sequence of component images at different focus settings brings with it the possibility of performing "on-the-fly" adjustment/optimization of imaging parameters per focus setting. In this context, in a particular embodiment of the invention, different members of the sequence of component images within said imaging step have different values of at least one imaging parameter (other than focus). For example, one might elect to (re-)adjust/correct one or more of image rotation, magnification scaling, image skew and lateral image displacement for each focus setting (or for a selection of focus settings) in the sequence $[F_n]$. In a more advanced approach, one could, for example, attempt to individually correct image distortion per component image/focus setting.

The raw image data acquired in the method according to the current invention can be mathematically processed in various ways. For good order, certain aspects of such processing will now be elucidated in more detail.

In tomography, a series of angular projections of an object is referred to as a sinogram. In a process conventionally referred to as "reconstruction", such a sinogram can be processed and converted into a corresponding composite image (spatially resolved image, 3D image, deconvolved image set) using various known mathematical techniques. For example:

SIRT: Simultaneous Iterative Reconstruction Technique.
See, for example:
http://www.vcipt.org/pdfs/wcipt1/s2_1.pdf
P. Gilbert, *Journal of Theoretical Biology*, Volume 36, Issue 1, July 1972, Pages 105-117.
DART: Discrete Algebraic Reconstruction Technique.
See, for example:
http://en.wikipedia.org/wiki/Algebraic_reconstruction_technique
http://www.emat.ua.ac.be/pdf/1701.pdf, and references therein.

For detailed information, reference is made (for example) to the following well-known book:

A. C. Kak and Malcolm Slaney, *Principles of Computerized Tomographic Imaging*, IEEE Press, 1999.

In particular, chapter 3 of said book, especially sections 3.2 and 3.3, describes how the so-called Fourier Slice Theorem can be used as the basis for a reconstruction procedure.

Other well-known terms/techniques in the field of sinogram reconstruction include WBP (Weighted Back Projection) and POCS (projection Onto Convex Sets), for example.

The skilled artisan in the field of TEM tomography will be familiar with these and other suitable mathematical reconstruction techniques.

It should be noted that the technique used in the current invention differs substantially from the method disclosed in European Patent Application EP 1 628 321 A2. In this latter document, a variety of test images is acquired at different focus settings for a given sample tilt value. These test images are then visually inspected by an operator, so as to determine which of them offers most satisfactory contrast. This "best-contrast" test image is then selected, and the other test images are discarded. The result is that, in subsequent mathematical reconstruction, only one "best-contrast" focus value is used per sample tilt value—unlike the current invention, which performs reconstruction on the basis of multiple focus values per sample tilt value. The result of the mathematical reconstruction in EP 1 628 321 is thus a 2D imaging sheet—rather than the 3D imaging cube of the current invention.

For good order, it should be noted in the context of this entire document that the fact that an image is formed as a consequence of passing a beam of particles through the sample does not restrict image formation to the use of transmitted particles; one may alternatively/supplementally form an image using scattered radiation or secondary radiation, for example.

The invention will now be elucidated in more detail on the basis of exemplary embodiments and the accompanying schematic drawings, in which:

FIG. 1 renders a longitudinal cross-sectional view of part of a charged-particle microscope (TEM) in which a method according to the present invention can be enacted.

Figure 2A:
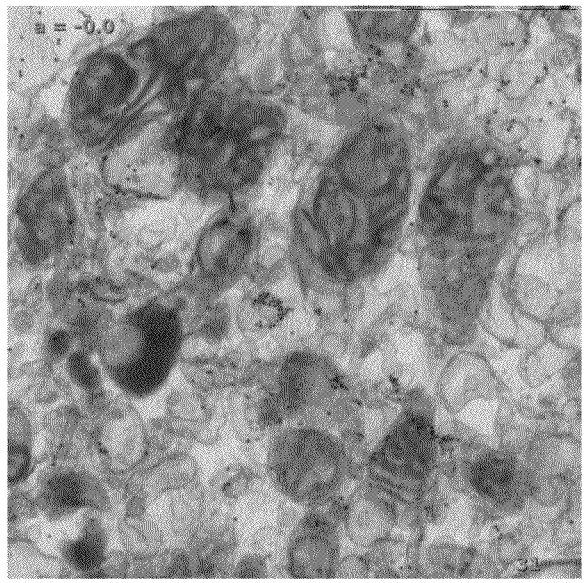
Figure 2B:
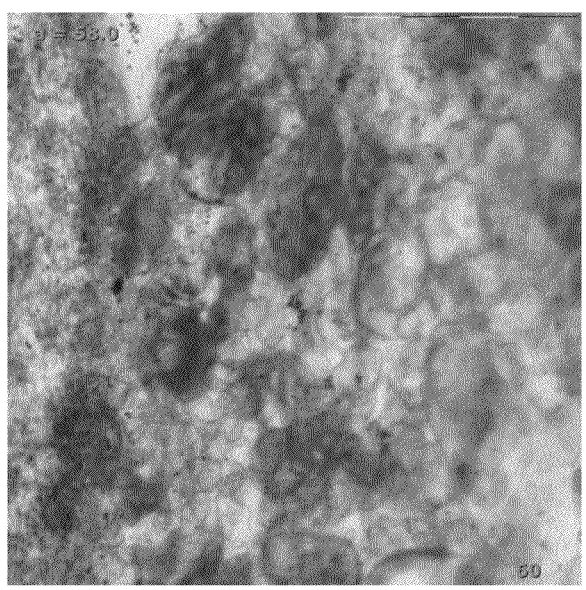
Figure 2C:
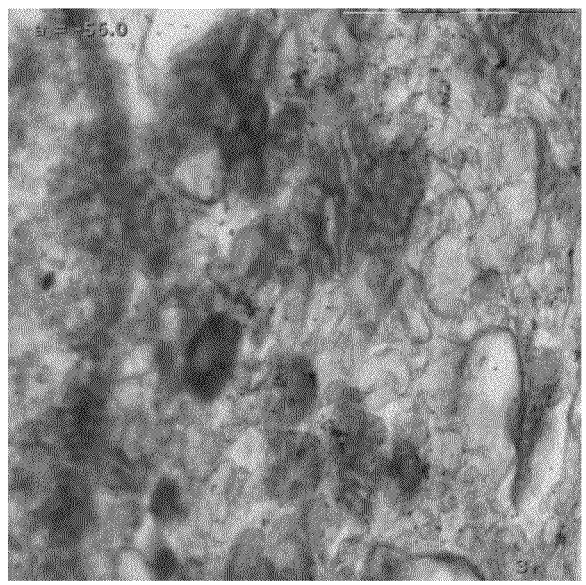

FIG. 2 illustrates the phenomenon of focus gradient for a non-tilted sample (FIG. 2A) as compared to a tilted sample (FIGS. 2B, 2C), and also illustrates the result of a change in focus setting for a tilted sample, whereby a region of best focus shifts from left (FIG. 2B) to right (FIG. 2C) as focus height is adjusted.

In the Figures, where relevant, corresponding parts are indicated using corresponding reference symbols.

Embodiment 1

FIG. 1 renders a highly schematic longitudinal cross-sectional view of a particular embodiment of a CPM in which the current invention can be applied. In the present instance, the CPM is a TEM.

The depicted TEM comprises a vacuum housing 120 that is evacuated via tube 121 connected to a vacuum pump 122. A particle source in the form of an electron gun 101 produces a beam of electrons along a particle-optical axis (imaging axis) 100. The electron source 101 can, for example, be a field emitter gun, a Schottky emitter, or a thermionic electron emitter. The electrons produced by the source 101 are accelerated to an adjustable energy of typically 80-300 keV (although TEMs using electrons with an adjustable energy of 50-500 keV, for example, are also known). The accelerated electron beam then passes through a beam limiting aperture/diaphragm 103 provided in a platinum sheet. To align the electron beam properly to the aperture 103, the beam can be shifted and tilted with the aid of deflectors 102, so that the central part of the beam passes through the aperture 103 along axis 100. Focusing of the beam can be achieved using magnetic lenses 104 of a condenser system, together with (part of the) final condenser lens 105. Deflectors (not depicted) are used to center the beam on a region of interest on a sample, and/or to scan the beam over the surface of the sample. In this schematic, functional depiction, the deflectors 102 are shown relatively high up in the CPM, and final condenser lens 105 is shown as being relatively small; however, the skilled artisan will appreciate that deflectors 102 may be much lower in the CPM (e.g. nested within the lens 105), and that item 105 may be much larger than depicted.

The sample to be examined is held by a sample holder 112 in such a manner that it can be positioned in the object plane 111 of projection system 106 (whose uppermost lens element is conventionally referred to as an objective lens). The sample holder 112 may offer various positional/motional degrees of freedom (one or more of translation(s), pitch, roll and yaw), and may also have temperature control functionality (heating or cryogenic). It may be a conventional type of sample holder for holding a static sample in a containment plane; alternatively, the sample holder 112 can be of a special type that accommodates a moving sample in a flow plane/channel that can contain a stream of liquid water or other solution, for example. The sample holder will generally be connected to a set of actuators (not depicted) so as to position/orient/move it as desired.

The sample is imaged by projection system (projection lens system, projection column) 106 onto fluorescent screen 107, and can be viewed through a window 108. The enlarged image formed on the screen typically has a magnification in the range $10^3 x$-$10^6 x$, and may show details as small as 0.1 nm or less, for example. The fluorescent screen 107 is connected to a hinge 109, and can be retracted/folded away such that the image formed by the projection system 106 impinges upon image detector 151 in detection subsystem 150. It is noted that, in such an instance, the projection system 106 may need to be (slightly) re-focused so as to form the image on the image detector 151 instead of on the fluorescent screen 107. It is further noted that the projection system 106 may additionally form intermediate images at intermediate image planes (not depicted).

The image detector 151 may, for example, comprise a Complementary Metal Oxide Semiconductor (CMOS) device, which can be used to detect impinging electrons. As an alternative to electron detection, one can also use a CMOS device that detects light—such as the light emitted by a Yttrium Aluminium Garnet (YAG) crystal (for example) that is bonded to the CMOS device, or connected thereto by optical fibers (for example). In such an indirect detector, the YAG crystal emits a number of photons when an electron hits the crystal, and a portion of these photons is detected by the CMOS device; in direct detectors, electrons impinge on the semiconductor chip of the CMOS device and generate electron/hole pairs, thereby forming the charge to be detected by the CMOS device. One could also consider using a Charge-Coupled Device (CCD) instead of a CMOS device; however, in the context of the current invention, the typically greater detection speed/sensitivity of the CMOS device will tend to make it preferable. The detector 151 is connected to a processing apparatus (controller) and display unit, which are not depicted in FIG. 1. Other subsystems of the CPM may also be connected to this and/or another controller, such as the source 101, various lens elements 104, 105, 106, actuators for controlling the position/orientation of sample holder 112, deflectors 102, 152, etc.

The image formed on the fluorescent screen 107 and on the image detector 151 is generally aberrated due (for example) to imperfections produced in the projection system 106. To correct such aberrations, various multipoles can be deployed in/near the projection system 106. Such multipoles are not depicted in FIG. 1, so as to avoid cluttering the drawing, but the skilled artisan will be familiar with their design, positioning and implementation.

Also depicted in FIG. 1 are deflection coils 152. These can, for example, be used to deflect transmitted electrons (traversing the sample) in a direction away from the optical axis 100 and toward an off-axis EELS detector (not depicted in FIG. 1; EELS=Electron Energy-Loss Spectroscopy). Alternatively, in a variant tool referred to as an EFTEM (Energy-Filtered TEM) the coils 152 may play the role of an energy "filter", whose purpose is to select which energy range of electrons will be admitted to the detector 151 at any given time; in this context, the coils 152 will "pass" certain electron energies while deflecting others aside.

It should be noted that FIG. 1 only shows a schematic rendition of a (simplified) TEM, and that, in reality, a TEM will generally comprise many more deflectors, apertures, etc.

In the context of the current invention, the apparatus of FIG. 1 may be employed as follows;

(i) By making appropriate adjustments to actuators connected to sample holder 112, its altitude angle and/or azimuth angle with respect to the particle-optical axis 100 can be varied; in this way, a sample attached to the holder 112 can be given various tilt values. If desired, the aforementioned controller can be pre-programmed with a series of different sample tilt values $\{T_m\}$ that are to be used in the course of a tomographic measurement; alternatively, one may choose such values manually.

(ii) The position of the sample holder 112 with respect to a focal point of the beam propagating along axis 100 can also be adjusted in various ways. Traditionally, this can be done by making adjustments to the optical power of one or more lens elements in the optical column, e.g. condenser lens 104/105 or projection (objective) lens 106. However, one could alternatively/supplementally use an actuator to make fine adjustments to the position of sample holder 112 parallel to the axis 100. As in item (i), the referenced controller can be pre-programmed with a sequence of different focus settings $[F_n]$ that are to be used in the course of a tomographic measurement according to the invention; alternatively, one may choose such values manually. It should be noted that the cardinality of the focus sequence $[F_n]$ will generally be different to that of the aforementioned tilt series $\{T_m\}$.

(iii) In conventional TEM tomography, for each tilt value $T_m$ from said tilt series, an imaging step is performed whereby a single image of the sample is captured by detector 151 at a single focus setting. However, in the current invention, said imaging step is more complex, in that a sequence of component images $[I_n]$ is captured by the detector 151, the sequence $[I_n]$ comprising one component image for each member of the focus sequence $[F_n]$. The imaging step according to the invention thus accrues a 3D imaging cube at each tilt value $T_m$ rather than just a 2D imaging sheet. Accordingly, for a given tilt series $\{T_m\}$, the method according to the present invention acquires a much larger and more data-rich sinogram than in the case of the prior art.

(iv) The sinogram resulting from step (iii) is subjected to a mathematical reconstruction procedure as set forth above, thus yielding a composite image of the sample that is three-dimensional/spatially resolved in depth. Because of the multiple-focus data acquisition approach used in step (iii), a selected layer/level in this reconstructed composite image will have improved resolution and a more predictable power spectrum compared to results from prior-art transmission tomography.

In the context of items (iii) and (iv), the skilled artisan will realize that, within a typical 3D imaging cube as referred to in (iii), the sample will occupy a tilt plane T that will, in general, not be parallel to any face of said cube. When processing such a cube in step (iv), data is preferably extracted from the cube so as to be grouped into planar slices parallel to T. This may, for example, be achieved by applying a suitable (tilt-dependent) coordinate transformation to the cube before processing it. The skilled artisan will readily grasp this point; however, for good order, more information on this topic can, for example, be gleaned from the book 3-*D Image Processing Algorithms* by Nikos Nikolaidis and Ioannis Pitas, ISBN 0471377368, October 2000, e.g. chapter/section 1.4.1.

Embodiment 2

FIG. 2 shows TEM imaging results on a biological sample. More particularly, these Figures serve to illustrate the effects of different focus settings when imaging a tilted sample. In each case, the plane of a given Figure (plane of the page) may be regarded as being a focal plane (FP) of a particle-optical column being used to image the sample onto a detector.

In FIG. 2A the sample is postured so that its surface S (distal from the sample holder on which it rests) is parallel to FP. As a result, all points on S are essentially in focus.

In FIG. 2B, the same sample is tilted in such a way that S subtends an angle with FP. As here depicted, the left region of FP is intercepted by S, so that this portion of the sample is in focus. The rest of S is located beneath (or above) FP, and is thus out of focus—whence the steadily increasing degree of blurring as one moves toward the right of FIG. 2B.

In FIG. 2C, surface S has been displaced (by a given increment) along an axis perpendicular to the plane of the drawing. As a result, regions of S that previously intercepted FP no longer do so, whereas other regions of S that did not previously intercept FP now do intercept it. More specifically, the right region of FP is now intercepted by S, so that this portion of the sample is in focus. The rest of S is located above (or below) FP, and is thus out of focus—whence the steadily increasing degree of blurring as one moves toward the left of FIG. 2C.

In the current invention, during each imaging step, several such increments are effected in the relative position of (tilted) S and FP, and an image of the sample is captured for each of the resulting focus settings.

We claim as follows:

1. A method of performing tomographic imaging of a sample in a charged-particle microscope, comprising the following steps:
   providing a beam of charged particles that propagate along a particle-optical axis;
   providing the sample on a sample holder that can be tilted relative to said beam;

in an imaging step, directing the beam through the sample so as to form and capture an image of the sample at an image detector;

repeating this procedure at each of a series of sample tilts so as to acquire a corresponding set of images;

in a reconstruction step, mathematically processing images from said set so as to construct a composite image of the sample, wherein:

in said imaging step, for a given sample tilt, a sequence of component images is captured at a corresponding sequence of focus settings;

in said reconstruction step, for at least one member of said series of sample tilts, multiple members of said sequence of component images are used in said mathematical image processing.

2. The method of claim 1, wherein, during said imaging step, the relative position of the particle-optical axis and the sample is kept substantially constant.

3. The method of claim 1, wherein, during said imaging step, the relative position of the particle-optical axis and the sample is varied by causing the beam to scan along the sample.

4. The method of claim 1, wherein, within said imaging step, different members of said sequence of component images have different values of at least one imaging parameter other than focus.

5. The method of claim 1, wherein the cardinality of the sequence of focus settings is not the same for all members of the series of sample tilts.

6. The method of claim 1, wherein, in said reconstruction step, for each member of said series of sample tilts, all captured component images are used in said mathematical image processing.

7. A charged-particle microscope comprising:
a charged-particle source, for producing a charged-particle beam that propagates along a particle-optical axis;
a sample holder, for holding and positioning a sample;
a charged-particle lens system, for directing said beam through the sample so as to form an image of the sample;
an image detector, for capturing said image in an imaging step;
an apparatus for adjusting a focus setting of the beam relative to the sample; and
a computer processor, for mathematically processing input images in a reconstruction step, so as to form an output reconstructed image,
which microscope is programmed to perform a method as claimed in claim 1.

8. The charged-particle microscope of claim 7, wherein, during said imaging step, the relative position of the particle-optical axis and the sample is kept substantially constant.

9. The charged-particle microscope of claim 7, wherein, during said imaging step, the relative position of the particle-optical axis and the sample is varied by causing the beam to scan along the sample.

10. The charged-particle microscope of claim 7, wherein, within said imaging step, different members of said sequence of component images have different values of at least one imaging parameter other than focus.

11. The charged-particle microscope of claim 7, wherein, the cardinality of the sequence of focus settings is not the same for all members of the series of sample tilts.

12. The charged-particle microscope of claim 7, wherein, in said reconstruction step, for each member of said series of sample tilts, all captured component images are used in said mathematical image processing.

13. A charged-particle microscope comprising
a charged-particle source, for producing a charged-particle beam that propagates along a particle-optical axis;
a sample holder, for holding and positioning a sample;
a charged-particle lens system, for directing said beam through the sample so as to form an image of the sample;
an image detector, for capturing said image in an imaging step;
an apparatus for adjusting a focus setting of the beam relative to the sample;
a computer processor, for mathematically processing input images in a reconstruction step, so as to form an output reconstructed image; and
a processing apparatus controller programmed to control the charged-particle microscope for:
providing a beam of charged particles that propagate along a particle-optical axis;
providing the sample on a sample holder that can be tilted relative to said beam;
in an imaging step, directing the beam through the sample so as to form and capture an image of the sample at an image detector;
repeating this procedure at each of a series of sample tilts so as to acquire a corresponding set of images;
in a reconstruction step, mathematically processing images from said set so as to construct a composite image of the sample,
wherein:
in said imaging step, for a given sample tilt, a sequence of component images is captured at a corresponding sequence of focus settings;
in said reconstruction step, for at least one member of said series of sample tilts, multiple members of said sequence of component images are used in said mathematical image processing.

14. The charged-particle microscope of claim 13, wherein the processing apparatus controller is programmed so that during said imaging step, the relative position of the particle-optical axis and the sample is kept substantially constant.

15. The charged-particle microscope of claim 13, wherein the processing apparatus controller is programmed so that during said imaging step, the relative position of the particle-optical axis and the sample is varied by causing the beam to scan along the sample.

16. The charged-particle microscope of claim 13, wherein the processing apparatus controller is programmed so that, within said imaging step, different members of said sequence of component images have different values of at least one imaging parameter other than focus.

17. The charged-particle microscope of claim 13, wherein the processing apparatus controller is programmed so that the cardinality of the sequence of focus settings is not the same for all members of the series of sample tilts.

18. The charged-particle microscope of claim 13, wherein the processing apparatus controller is programmed so that in said reconstruction step, for each member of said series of sample tilts, all captured component images are used in said mathematical image processing.

\* \* \* \* \*